United States Patent [19]

Wellershaus

[11] Patent Number: 5,156,632
[45] Date of Patent: Oct. 20, 1992

[54] JOINTLESS PROSTHETIC FOOT

[75] Inventor: Ulf Wellershaus, Duderstadt, Fed. Rep. of Germany

[73] Assignee: Otto Bock Orthopaedische Industrie Besitz- und Verwaltungs-Kommanditgesellschaft, Duderstadt, Fed. Rep. of Germany

[21] Appl. No.: 789,651

[22] Filed: Nov. 8, 1991

[30] Foreign Application Priority Data

Nov. 29, 1990 [DE] Fed. Rep. of Germany ....... 4038063

[51] Int. Cl.$^5$ .............................................. A61F 2/66
[52] U.S. Cl. ........................................ 623/55; 623/49; 623/53
[58] Field of Search .................... 623/53–56, 623/47–50, 52

[56] References Cited

U.S. PATENT DOCUMENTS

| | | | |
|---|---|---|---|
| 2,556,525 | 6/1951 | Drennon | 623/49 |
| 3,335,428 | 8/1967 | Gajdos | 623/55 |
| 5,062,859 | 11/1991 | Naeder | 623/55 |
| 5,064,438 | 11/1991 | Naeder | 623/53 X |

OTHER PUBLICATIONS

"Development and Preliminary Evaluation of the VA Seattle Foot" by E. M. Burgess et al, Journal of Rehabilitation Research and Development, vol. 22, No. 3, BRP10–42, pp. 75–84.

Primary Examiner—Ronald Frinks
Attorney, Agent, or Firm—Foley & Lardner

[57] ABSTRACT

A prosthetic foot includes a prosthesis body having a toe region disposed in a front part of the prosthetic foot, and a one-piece insert which is provided in the prosthesis body and which absorbs and transmits stresses imposed on the prosthesis body. The insert enables at least a plantar and dorsal deflection as well as axial compression of the prosthesis body, and has an approximately S-shaped design in the longitudinal section of the prosthetic foot. The insert includes a top horizontal section which forms a top edge of the prosthetic foot, and a bottom horizontal section which is of an extended construction compared with the top section and which has a free end which extends into the toe region of the prosthesis body, so that a high elasticity and a high energy storage capacity of the front part of the prosthetic foot are achieved. A front inclined section extends at an obtuse angle from the top section to form a rigid angular element. A central section functions as a leaf spring and has a front end which is connected to a lower end of the angular element and has a rear end. An approximately semi-circular rear connecting section is connected to the bottom section and to the rear end of the central section.

20 Claims, 4 Drawing Sheets

JOINTLESS PROSTHETIC FOOT

BACKGROUND OF THE INVENTION

The invention relates to a jointless prosthetic foot having a resilient foot insert which is provided inside the prosthesis body, which absorbs and transmits the prosthetic stresses, and which has a top horizontal section and a bottom horizontal section. The top horizontal section forms the top edge of the prosthetic foot and offers a connection possibility with the prosthesis. The bottom section is of extended construction compared to the top section and extends with its free end into the toe region to achieve a high elasticity of the front part of the foot in conjunction with a high energy storage capacity when the front part of the foot is stressed.

A foot of the type mentioned above has become known through the so-called Seattle foot (see VETERANS ADMINISTRATION—JOURNAL OF REHABILITATION RESEARCH AND DEVELOPMENT, Vol. 22, No. 3, BPR 10-42, pages 75-84, in particular FIG. 6).

The function of a prosthetic foot depends substantially on its elastic properties. These are determined by material, design and arrangement of the elastic components used.

Depending on the intended area of application, which can range from normal walking on a level surface up to sporting use, such as jogging, running, jumping, depending on the desires of the amputee, the requirements of such components are widely varied. More particularly, the requirements of the working capacity and the variation of spring characteristics, which are closely associated with the working capacity, can be widely varied when stressed and unstressed to meet the desires of the amputee.

The more recent developments of jointless prosthetic feet for use in as wide an area of application as possible deviate from the conventional concept of the so-called SACH foot in that they supplement the rigid core of the foot in the front region of the foot with spring elements or replace it completely by such spring elements, which is the case with the SEATTLE foot. These modifications are effected in order to improve the elasticity of the front part of the foot and thus also the energy storage capacity when the front part of the foot is stressed. In this case, the elasticity of the heel is achieved in a largely unchanged design by a foam wedge in the heel region.

OBJECT AND SUMMARY OF THE INVENTION

The underlying object of the invention is to develop a prosthetic foot of the design explained above having improved properties.

In accordance with a first aspect of the invention, a prosthetic foot is provided which includes a prosthesis body having a toe region disposed in a front part of the prosthetic foot, and a one-piece insert which is provided in the prosthesis body and which absorbs and transmits stresses imposed on the prosthesis body. The insert enables at least a plantar and dorsal deflection as well as axial compression of the prosthesis body, and has an approximately S-shaped design in the longitudinal section of the prosthetic foot. The insert includes a top horizontal section which forms a top edge of the prosthetic foot, and a bottom horizontal section which is of an extended construction compared with the top section and which has a free end which extends into the toe region of the prosthesis body, so that a high elasticity and a high energy storage capacity of the front part of the prosthetic foot are achieved. A front inclined section extends at an obtuse angle from the top section to form a rigid angular element. A central section functions as a leaf spring and has a front end which is connected to a lower end of the angular element and has a rear end. An approximately semi-circular rear connecting section is connected to the bottom section and to the rear end of the central section.

In accordance with another aspect of the invention, a bulge is formed on an upper surface of the bottom section under a connection area at which the central section is connected to the angular element, and an air gap is formed between the bulge and the connection area. The air gap has a slight wedge formation and opens toward the front of the prosthetic foot.

In accordance with yet another aspect of the invention, additional resilient components are connected to the insert, and all spring characteristics of the prosthetic foot are determined by the insert and the additional resilient components. One of the resilient components is provided on the bottom section and supports the rigid angular element, and one of the resilient components is enclosed by the rear connecting section. In addition, a wedge-shaped space is formed between the central section and the bottom section, and one of the resilient components is provided in the space and is enclosed between the front inclined section and the central section.

In accordance with still another aspect of the invention, a flection limiter is provided in the free end of the top section. The flection limiter comprises a pin having a lower end secured to the rear end of the central section and having an upper end which extends through a recess in the top section and which terminates in a stop which limits movement of the top section.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The above and further objects of the invention will become more readily apparent as the invention is more clearly understood from the detailed description to follow, reference being had to the accompanying drawings in which like reference numerals represent like parts throughout, and in which.

DETAILED DESCRIPTION OF THE PREFERRED EMBODIMENTS

Figure 1:
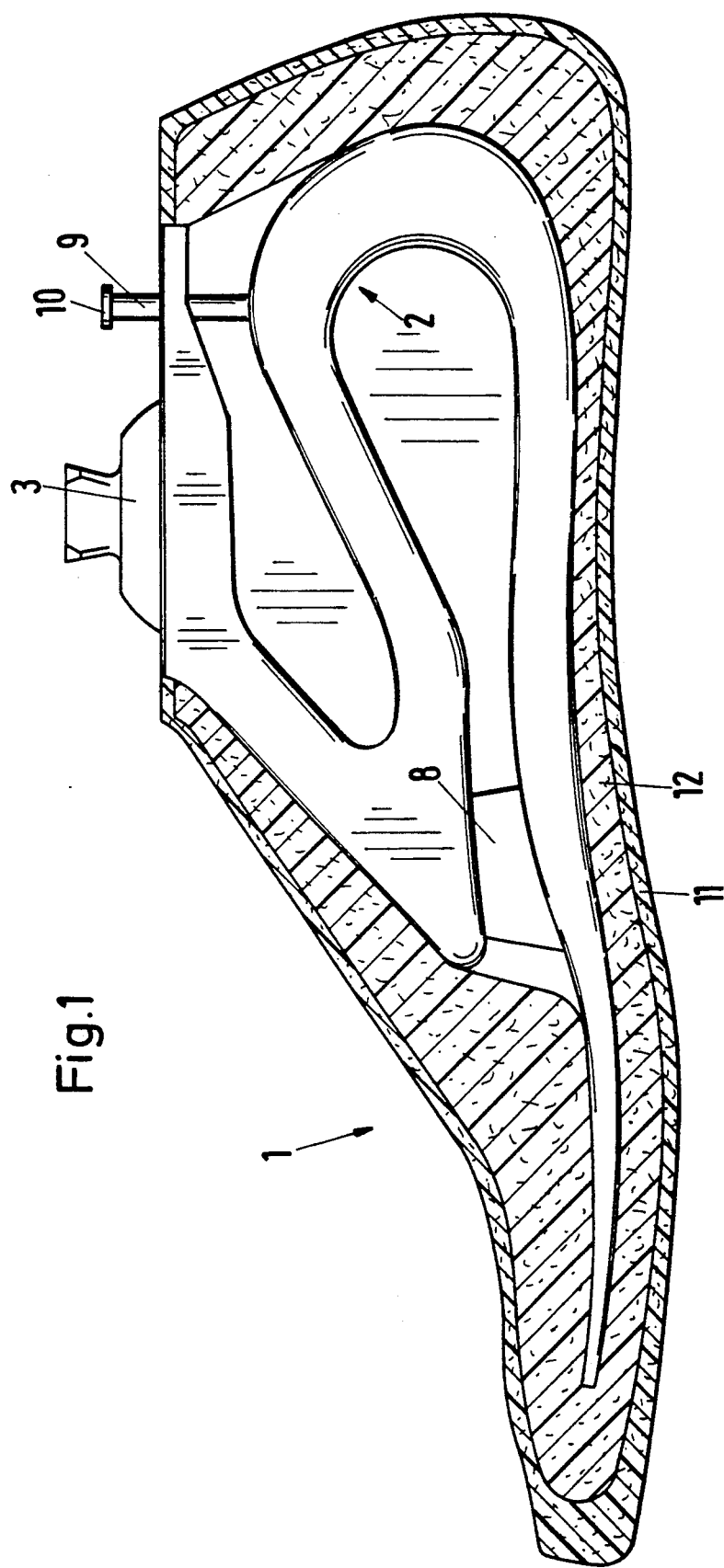
FIG. 1 shows a vertical longitudinal section through a jointless prosthetic foot with a resilient foot insert.

The primary object of the invention is achieved in that the one-piece foot insert is provided which enables at least a plantar and dorsal flection as well as an axial compression. The insert has an approximately S-shaped design in the longitudinal section of the foot. The top section forms, with a front inclined section connected to it at an obtuse angle, an altogether rigid angular element. A central section is connected to the lower end of the angular element. The central section is similar to a leaf spring and at its rear end, is connected to the bottom section via an approximately semi-circular connecting section.

In order to obtain a more natural movement for the prosthesis wearer, it is expedient for the lower end of the rigid angular element to extend forward approximately into the area of the metatarsophalangeal joints.

In order to shift the flection of the bottom section of the foot insert further forward in the event of an increasing angle of the front part of the foot, it is advantageous for the bottom section of the foot insert to have an upper bulge. The surface of the connection area lies above the upper bulge. The upper bulge and the surface of the connection area enclose an air gap which opens toward the front in a slight wedge formation.

According to the invention, the foot insert should be designed in such a way that the top section of the foot insert can be twisted in a horizontal plane relative to the bottom section. That is to say, the foot insert allows a torsion, and consequently a rotation, of the prosthetic foot about a vertical axis. In this case, it is also advantageous if the top section of the foot insert can be twisted, in the frontal plane lying perpendicular and transverse to the direction of walking, relative to the bottom section for adaptation to inclinations transverse to the direction of walking. According to the invention, it is possible for the resilient properties (spring characteristics) determining the force/path characteristic and the angle/moment characteristic of the swivel movements and deformations to be determined solely by the S-shaped foot insert. However, it is also possible for the spring characteristics to be achieved by the interaction of the S-shaped foot insert with additional resilient components.

The plantar flection is achieved by reducing the angle enclosed between the front inclined section and the central section in a plane perpendicular to the pelvis and parallel to the direction of walking. The dorsal flection is produced by reducing the distance between the lower end of the front inclined section and the upper surface of the bottom section of the foot insert.

Upon stressing, in order to prevent too great a spreading apart of the top section of the foot insert with respect to the central section acting as a leaf spring, it is advantageous for the free end of the top section of the foot insert to be provided with a flection limiter.

The prosthesis body preferably forms a one-piece cosmetic cover which encloses all of the functional elements and which has no securing elements on the outside. In this case, the prosthesis body can be designed in such a way that it provides a partial supporting function for the foot insert in the final stage of the standing phase. It is particularly advantageous if the prosthesis body is enclosed completely, except for its top connection surface, by a skin-forming outer layer of foamed plastic, which layer encloses an inner foot of foamed plastic extending into the toe region. The above-noted features will be explained in greater detail below.

The jointless prosthetic foot shown in FIG. 1 has a prosthesis body 1 enclosing a resilient foot insert 2, which absorbs and transmits the prosthetic stresses, is made in one piece, and enables at least a plantar and dorsal flection as well as an axial compression.

Viewed in the longitudinal direction of the foot, the foot insert 2 has an approximately S-shaped design. The top horizontal section 2a forms the top edge of the prosthetic foot and is provided with a foot adapter 3 for detachable connection to a prosthesis. A front inclined section 2b is connected to top section 2a at an obtuse angle. The top and inclined sections form an altogether rigid angular element, at the lower end 4 of which there is connected a central section 2c which is like a leaf spring. This latter section 2c is connected at its rear end to a bottom section 2e via an approximately semi-circular connecting section 2d. Bottom section 2e is of extended construction compared to the top section 2a and extends with its free end into the toe region of foot 1 so as to achieve a high elasticity of the front part of the foot in conjunction with a high energy storage capacity when the front part of the foot is stressed. The lower contour of the bottom horizontal section 2e is adapted to match the contour of the underside of the foot 1. In addition, the bottom section 2e has an upper bulge 5 located under the connection area of the central section 2c to the lower end 4 of the rigid angular element 2a, 2b. The upper bulge 5 and the surface 6 of the connection area lying above the upper bulge enclose an air gap 7 which opens toward the front of the foot 1 in a slight wedge formation. In this case, the lower end 4 of the rigid angular element 2a, 2b extends forward approximately into the area of the metatarsophalangeal joints at which the bottom section 2e flexes during normal use.

At its lower end 4, the rigid angular element 2a, 2b bears on the bottom section 2e via a resilient element 8. This resilient element 8 is compressed upon stressing, as can be seen in FIG. 3. In the embodiment shown in FIGS. 1 to 3, the rear connecting section 2d of the foot insert 2 is of rigid design. The foot insert 2 is thus made up of a substantially rigidly designed angular part 2a, 2b, a central leaf spring (central section 2c), a bottom leaf spring (bottom section 2e) and a connection part (connecting section 2d) connecting the two leaf springs rigidly to one another at their rear ends. In this design, the foot insert 2 can be made of plastic. A substantially more natural movement for the prosthesis wearer is obtained by means of the lower end 4 of the rigid angular element 2a, 2b extending relatively far forward. On account of the shaping of the previously described air gap 7, the flection of the bottom section 2e shifts forward in the event of an increasing angle of the front part of the foot. This flection first arises in a central area and then moves to the bearing area between the lower end 4 of the rigid angular element 2a, 2b and the upper bulge 5 of the bottom section 2e and, in the event of a greater angle of the front part of the foot, shifts further forward into an area of the bottom section 2e which, as intended, has a cross-section tapering toward the front or a material thickness decreasing toward the front.

Figure 2:
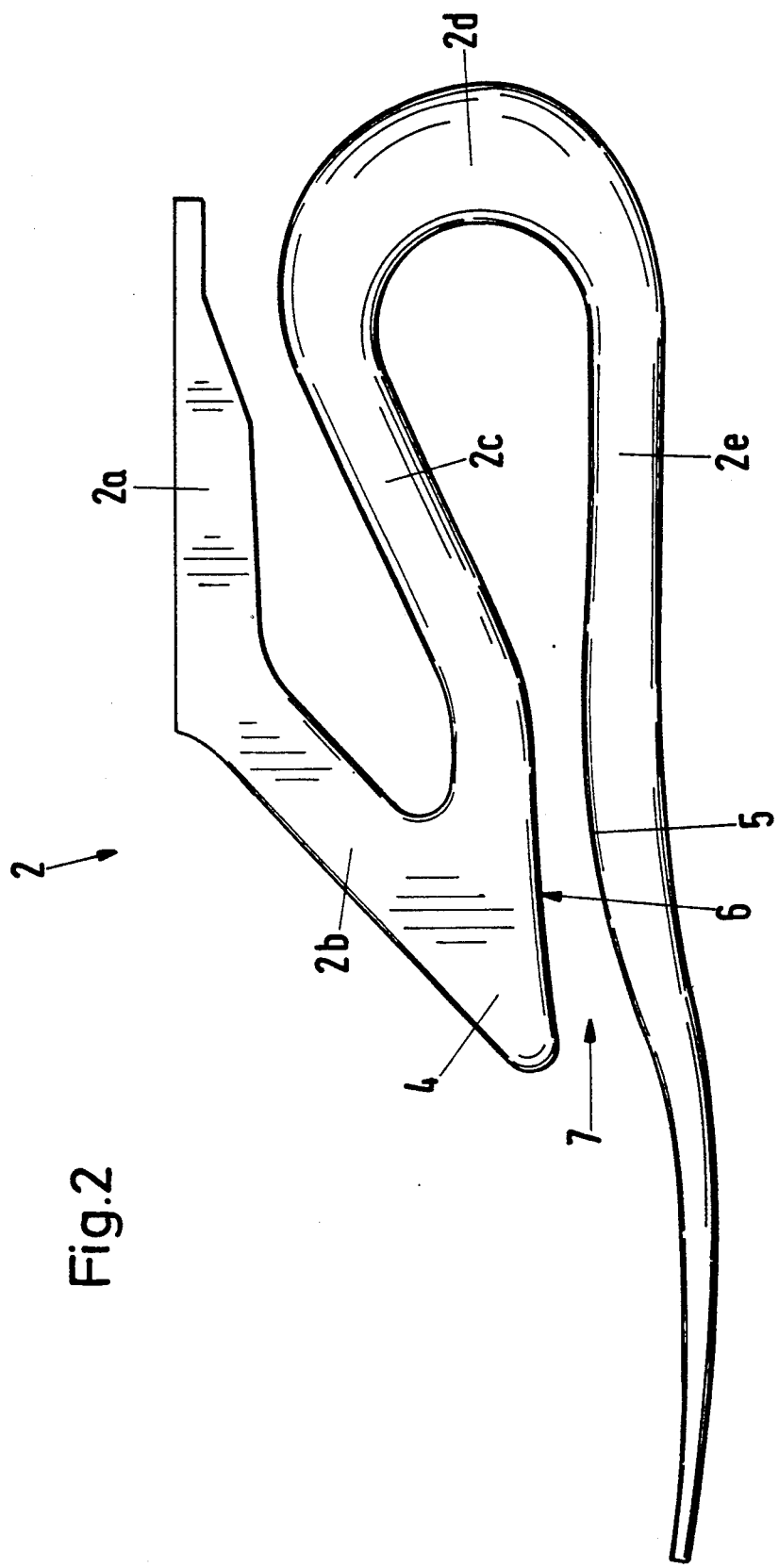
FIG. 2 shows the foot insert according to FIG. 1 in a separate representation.
Figure 3:
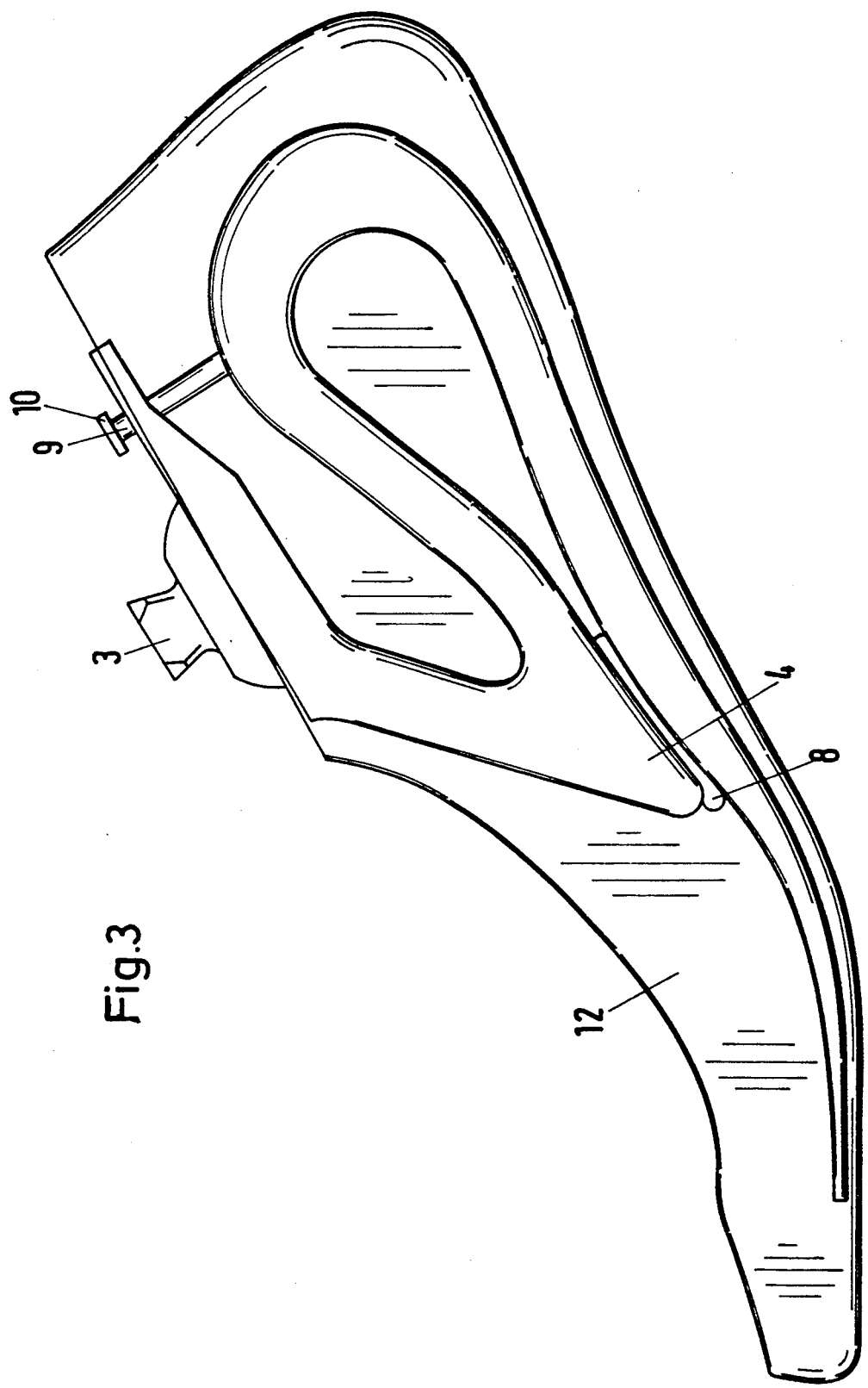
FIG. 3 schematically shows the prosthetic foot according to FIG. 1 in a stressing phase.

Upon stressing, in order to prevent too great a spreading apart of the top section 2a with respect to the central section 2c acting as a leaf spring, a flection limiter is provided in the exemplary embodiment according to FIGS. 1 to 3. This limiter consists of a pin 9 which is secured with its lower end on the rear end of the central section 2c of the foot insert 2, is guided relatively displaceably through a recess in the top section 2a and has a stop 10 for the top section 2a at its other end projecting above the top section 2a.

According to FIG. 1, the prosthesis body 1 forms a one-piece cosmetic cover which encloses all of the functional elements, has no securing elements on the outside, extends as far as the ankle area and, at the top, terminates flush with the top section 2a. This cosmetic cover is designed in such a way that it provides a partial supporting function for the foot insert 2 in the final stage of the standing phase. This foot insert 2 can be pushed into the cosmetic cover in the manner of a shoetree with the aid of a special instrument which is, per se, well known. In the cover, the foot insert then locks itself and is thus prevented from inadvertently falling out of the cosmetic cover.

The cosmetic cover forming the prosthesis body 1 is enclosed completely, except for its top connection surface, by a skin-forming outer layer of foamed plastic 11 which encloses an inner foot 12 of foamed plastic extending into the toe region. The outer foamed plastic layer 11 has a specific mass of approximately 0.4 g/cm$^3$ and restoring forces which are small compared to the restoring forces of the inner foot 12. The foamed plastic forming the inner foot 12 has a specific mass of 0.6 to 1.0 g/cm$^3$.

Figure 4:
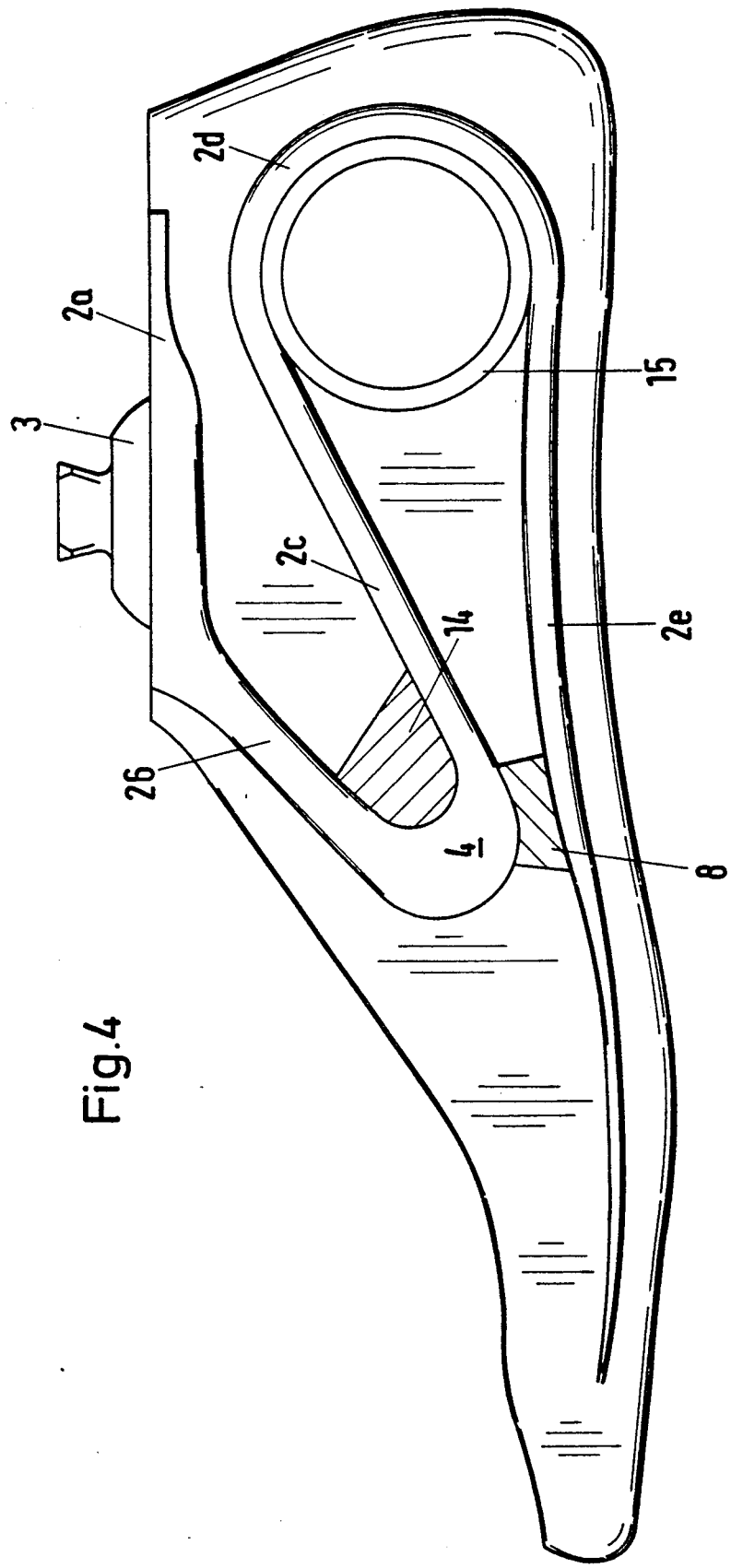
FIG. 4 shows a modified embodiment in a representation according to FIG. 1.

FIG. 4 shows a slightly modified embodiment, in which the foot insert 2 consists preferably of a carbon fiber material. In this case, a resilient support 14 is provided in the wedge-shaped space 13 of the foot insert 2 enclosed between the front inclined section 2b and the central section 2c. The rear connecting section 2d of the foot insert 2 encloses a tubular support 15 which, if appropriate, may also have resilient properties.

In both embodiments of the foot insert 2, the top section 2a can be twisted in a horizontal plane relative to the bottom section 2e, and thus permits a torsion, and consequently a rotation, of the prosthetic foot about a vertical axis. In addition, the top section 2a of the foot insert 2 can be twisted relative to the bottom section 2e in the frontal plane lying perpendicular and transverse to the direction of walking, i.e., to the longitudinal plane of the foot. This twisting allows the insert to adapt to inclinations transverse to the direction of walking.

What is claimed is:

1. A jointless prosthetic foot for connection to a prosthesis, said prosthetic foot comprising:
   (A) a prosthesis body having a toe region disposed in a front part of said prosthetic foot; and
   (B) a one-piece insert which is provided in said prosthesis body and which absorbs and transmits stresses imposed on said prosthesis body, said insert enabling at least a plantar and dorsal deflection as well as axial compression of said prosthesis body, said insert having an approximately S-shaped design in the longitudinal section of said prosthetic foot, said insert including
      a top horizontal section which forms a top edge of said prosthetic foot and which is connectable to said prosthesis,
      a bottom horizontal section which is of an extended construction compared with said top section and which has a free end which extends into said toe region of said prosthesis body, whereby a high elasticity and a high energy storage capacity of said front part of said prosthetic foot are achieved,
      a front inclined section extending at an obtuse angle from said top section, said top section and said inclined section forming a rigid angular element,
      a central section having a front end which is connected to a lower end of said angular element and having a rear end, said central section functioning as a leaf spring, and
      an approximately semi-circular rear connecting section which is connected to said bottom section and to said rear end of said central section.

2. The prosthetic foot as claimed in claim 1, wherein said angular element has a lower end which extends forward approximately in the area of metatarsophalangeal joints.

3. The prosthetic foot as claimed in claim 1, wherein a bulge is formed on an upper surface of said bottom section under a connection area at which said central section is connected to said angular element, an air gap being formed between said bulge and said connection area, said air gap having a slight wedge formation and opening toward the front of said prosthetic foot.

4. The prosthetic foot as claimed in claim 1, wherein said top section can be twisted in a horizontal plane relative to said bottom section, thereby allowing a torsion and consequently a rotation of said prosthetic foot about a vertical axis.

5. The prosthetic foot as claimed in claim 4, wherein said top section can be twisted relative to said bottom section in a frontal plane lying perpendicular and transverse to a direction of walking.

6. The prosthetic foot as claimed in claim 5, wherein the resilient properties determining a force/path characteristic and angle/moment characteristic of said rotations and said flection of said prosthetic foot are determined solely by said insert.

7. The prosthetic foot as claimed in claim 1, further comprising additional resilient components connected to said insert, wherein all spring characteristics of said prosthetic foot are determined by said insert and said additional resilient components.

8. The prosthetic foot as claimed in claim 7, wherein one of said resilient components is provided on said bottom section and supports said rigid angular element.

9. The prosthetic foot as claimed in claim 7, wherein a wedge-shaped space is formed between said central section and said bottom section and one of said resilient components is provided in said space and is enclosed between said front inclined section and said central section.

10. The prosthetic foot as claimed in claim 7, wherein one of said resilient components is enclosed by said rear connecting section.

11. The prosthetic foot as claimed in claim 10, wherein said one resilient component is tubular in shape.

12. The prosthetic foot as claimed in claim wherein said top section has a free end, and further comprising a flection limiter provided in said free end of said top section.

13. The prosthetic foot as claimed in claim 12, wherein said top section has a recess formed therein, and wherein said flection limiter comprises a pin having a lower end secured to said rear end of said central section and having an upper end which extends through said recess in said top section and which terminates in a stop which limits movement of said top section.

14. The prosthetic foot as claimed in claim 1, further comprising a foot adapter provided on said top section.

15. The prosthetic foot as claimed in claim 1, wherein said bottom section has a lower contour which matches the contour of an underside of said prosthetic foot.

16. The prosthetic foot as claimed in claim 1, wherein said prosthesis body comprises a foot-shaped foamed article in which said insert is imbedded.

17. The prosthetic foot as claimed in claim 1, wherein said prosthesis body forms a one-piece cosmetic cover enclosing said insert.

18. The prosthetic foot as claimed in claim 17, further comprising a skin-forming outer layer of foamed plastic which encloses all of said prosthesis body except for a top connection surface thereof, and wherein said prosthesis body includes an inner foot of foamed plastic extending into said toe region.

19. The prosthetic foot as claimed in claim 18, wherein said outer layer has a specific mass of approximately 0.4 g/cm$^3$ and restoring forces which are smaller than those of said inner foot.

20. The prosthetic foot as claimed in claim 18, wherein said inner foot has a specific mass of between 0.6 and 1.0 g/cm$^3$.

* * * * *